(12) United States Patent
Jove et al.

(10) Patent No.: US 9,512,076 B2
(45) Date of Patent: Dec. 6, 2016

(54) INDIRUBIN DERIVATIVES AND USES THEREOF IN TREATING CHRONIC MYELOGENOUS LEUKEMIA

(71) Applicant: CITY OF HOPE, Duarte, CA (US)

(72) Inventors: Richard Jove, Duarte, CA (US); Sangkil Nam, Duarte, CA (US); Alexios-Leandros Skaltsounis, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 6 days.

(21) Appl. No.: 13/758,921

(22) Filed: Feb. 4, 2013

(65) Prior Publication Data

US 2013/0210834 A1 Aug. 15, 2013

Related U.S. Application Data

(60) Provisional application No. 61/594,934, filed on Feb. 3, 2012, provisional application No. 61/676,267, filed on Jul. 26, 2012.

(51) Int. Cl.
*C07D 209/40* (2006.01)
*C07D 403/14* (2006.01)
*C07D 209/34* (2006.01)

(52) U.S. Cl.
CPC .......... *C07D 209/40* (2013.01); *C07D 209/34* (2013.01); *C07D 403/14* (2013.01)

(58) Field of Classification Search
CPC ........................... C07D 209/34; C07D 209/40
See application file for complete search history.

(56) References Cited

U.S. PATENT DOCUMENTS

2011/0136808 A1 6/2011 Meijer et al.

OTHER PUBLICATIONS

Aichberger, K. J., et al., "Identification of mcl-1 as a BCR/ABL-Dependent Target in Chronic Myeloid Leukemia (CML): Evidence for Cooperative Antileukemic Effects of Imatinib and mcl-1 Antisense Oligonucleotides," Blood 105:3303-3311 (2005).
Benekli, M., et al., "Signal Transducer and Activator of Transcription Proteins in Leukemias," Blood 101:2940-2954 (2003).
Bromann, P. A., et al., "The Interplay Between Src Family Kinases and Receptor Tyrosine Kinases," Oncogene 23:7957-7968 (2004).
Bromberg, J. F., et al., "Stat3 as an Oncogene," Cell 98:295-303 (1999).
Buettner, R., et al., "Activated STAT Signaling in Human Tumors Provides Novel Molecular Targets for Therapeutic Intervention," Clin. Cancer Res. 8:945-954 (2002).
Carlesso, N., et al., "Tyrosyl Phosphorylation and DNA Binding Activity of Signal Transducers and Activators of Transcription (STAT) Proteins in Hematopoietic Cell Lines Transformed by Bcr/Abl," J. Exp. Med. 183:811-820 (1996).
Donato, N. J., et al.,"BCR-ABL Independence and LYN Kinase Overexpression in Chronic Myelogenoud Leukemia Cells Selected for Resistance to STI571," Blood 101:690-698 (2003).
Eisenbrand, G., et al., "Molecular Mechanisms of Indirubin and Its Derivatives: Novel Anticancer Moleculres with Their Origin in Traditional Chinese Phytomedicine," J. Cancer Res. Clin. Oncol. 130:627-635 (2004).
Gesbert, F., et al., "Bcr/Abl Activates Transcription of the Bcl-X Gene Through STAT5," Blood 96:2269-2276 (2000).
Haura, E. B., et al., "Mechanisms of Disease: Insights into the Emerging Role of Signal Transducers and Activators of Transcription in Cancer," Nat. Clin. Pract. Oncol. 2(6):315-324 (2005).
Herrington, J., et al., "The Role of STAT Proteins in Growth Hormone Signaling," Oncogene 19:2585-2597 (2000).
Hoessel, R., et al., "Indirubin, the Active Constituent of a Chinese Antileukaemia Medicine, Inhibits Cyclin-Dependent Kinases," Nat. Cell Biol. 1:60-67 (1999).
Holtz, M. S., et al., "Imatinib Mesylate (STI571) Inhibits Growth of Primitive Malignant Progenitors in Chronic Myelogenous Leukemia Through Reversal of Abnormally Increased Proliferation," Blood 99:3792-3800 (2002).
Horita, M., et al., "Blockade of the Bcr-Abl Kinase Activity Induces Apoptosis of Chronic Myelogenous Leukemia Cells by Suppressing Signal Transducer and Activator of Transcription 5-Dependent Expression of Bcl-xL," J. Exp. Med. 191(6):977-984 (2000).
Huang, M., et al., "Inhibition of Bcr-Abl Kinase Activity by PD180970 Blocks Constitutive Activation of Stat5 and Growth of CML Cells," Oncogene 21:8804-8816 (2002).
Klejman, A., et al., "The Src Family Kinase Hck Couples BCR/ABL to STAT5 Activation in Myeloid Leukemia Cells," EMBO J. 21(21):5766-5774 (2002).
Konig, H., et al., "Effects of Dasatinib on Src Kinase Activity and Downstream Intracellular Signaling in Primitive Chronic Myelogenous Leukemia Hematopoietic Cells," Cancer Res. 68:9624-9633 (2008).

(Continued)

*Primary Examiner* — Kamal Saeed
(74) *Attorney, Agent, or Firm* — Perkins Coie LLP; Yingli Wang

(57) ABSTRACT

Indirubin is the major active anti-tumor component of a traditional Chinese herbal medicine used for treatment of chronic myelogenous leukemia (CML). One aspect of the invention relates to a method of treating CML using at least one indirubin derivative compound or a pharmaceutical composition thereof. Indirubin derivatives (IRDs) potently inhibited Signal Transducer and Activator of Transcription 5 (Stat5) protein in CML cells. Compound IRD 810 inhibits Bcr-Abl/Stat5 or Src/Stat5 signaling in human KCL-22 CML and imatinib-resistant human KCL-22 CML cells expressing the T315I mutant Bcr-Abl. Previous studies indicate that SFKs cooperate with Bcr-Abl to activate downstream Stat5 signaling. Activation of Stat5 was strongly blocked by IRD 810 in CML cells. IRDs disclosed herein have been identified as potent inhibitors of Bcr-Abl/Stat5 or SFK/Stat5 signaling pathway. IRDs disclosed herein are new therapeutics for wild type or T315I mutant Bcr-Abl-positive CML patients, and may also treat other solid tumors, including prostate cancer and lymphoma.

3 Claims, 11 Drawing Sheets

(56) References Cited

OTHER PUBLICATIONS

Lionberger, J. M., et al., "Transformation of Myeloid Leukemia Cells to Cytokine Independence by Bcr-Abl is Suppressed by Kinase-Defective Hck," J. Biol. Chem. 275(24):18581-18585 (2000).

Marko, D., et al., "Inhibition of Cyclin-Dependent Kinase 1 (CDK1) by Indirubin Derivatives in Human Tumour Cells," British J. Cancer 84(2):283-289 (2001).

Nam, S., et al., "Indirubin Derivatives Inhibit Stat3 Signaling and Induce Apoptosis in Human Cancer Cells," PNAS 102 (17):5998-6003 (2005).

Nam, S., et al., "Action of the Src Family Kinase Inhibitor, Dasatinib (BMS-354825), on Human Prostate Cancer Cells," Cancer Res. 65:9185-9189 (2005).

Nam, S., et al., "Dasatinib (BMS-354825) Inhibits Stat5 Signaling Associated with Apoptosis in Chronic Myelogenous Leukemia Cells," Mol. Cancer Ther. 6:1400-1405 (2007).

Nelson, E. A., et al., "Identification of Human STAT5-Dependent Gene Regulatory Elements Based on Interspecies Homology," J. Biol. Chem. 281(36):26216-26224 (2006).

Nieborowska-Skorska, M., et al., "Signal Transducer and Activator of Transcription (STAT)5 Activation by BCR/ABL is Dependent on Intact Src Homology (SH)3 and SH2 Domains of BCR/ABL and Is Required for Leukemogenesis," J. Exp. Med. 189(8):1229-1242 (1999).

Parsons, S. J., et al., "Src Family Kinases, Key Regulators of Signal Transduction," Oncogene 23:7906-7909 (2004).

Ptasznik, A., et al., "Short Interfering RNA (siRNA) Targeting the Lyn Kinase Induces Apoptosis in Primary, and Drug-Resistant, BCR-ABL1 (+) Leukemia Cells," Nat. Med. 10(11):1187-1189 (2004).

Quintas-Cardama, A., et al., "Dasatinib (BMS-354825) is Active in Philidelphia Chromosome-Positive Chronic Myelogenous Leukemia After Imatinib and Nilotinib (AMN107) Therapy Failure," Blood 109:497-499 (2007).

Shah, N. P., et al., "Overriding Imatinib Resistance with a Novel ABL Kinase Inhibitor," Science 305:399-401 (2004).

Silva, C. M., et al., "Role of STATs as Downstream Signal Transducers in Src Family Kinase-Mediated Tumorigenesis," Oncogene 23:8017-8023 (2004).

Vougogiannopoulou, K., et al., "Soluble 3', 6-Substituted Indirubins with Enhanced Selectivity Towards Glycogen Synthase Kinase-3 Alter Circadian Period," J. Med. Chem. 51(20):6421-6431 (2008).

Wilson, M. B., et al., "Selective Pyrrolo-Pyrimidine Inhibitors Reveal a Necessary Role for Src Family Kinases in Bcr-Abl Signal Transduction and Oncogenesis," Oncogene 21:8075-8088 (2002).

Wu, J., et al., "Lyn Regulates BCR-ABL and Gab2 Tyrosine Phosphorylation and c-Cbl Protein Stability in Imatinib-Resistant Chronic Myelogenous Leukemia Cells," Blood 111:3821-3829 (2008).

Xiao, Z., et al., "Indirubin and Meisoindigo in the Treatment of Chronic Myelogenous Leukemia in China," Leuk. Lymphoma 43(9):1763-1768 (2002).

Yu, H., et al., "The STATs of Cancer—New Molecular Targets Come of Age," Nat. Rev. Cancer 4:97-105 (2004).

Yu, H., et al., "STATs in Cancer Inflammation and Immunity: A Leading Role for STAT3," Nat. Rev. Cancer 9:798-809 (2009).

Yuan, H., et al., "BCR-ABL Gene Expression Is Required for Its Mutations in a Novel KCL-22 Cell Culture Model for Acquired Resistance of Chronic Myelogenous Leukemia," J. Biol. Chem. 285(7):5085-5096 (2010).

Zhou, J., et al., "Enhanced Activation of STAT Pathways and Overexpression of Survivin Confer Resistance of FLT3 Inhibitors and Could Be Therapeutic Targets in AML," Blood 113:4052-4062 (2009).

| IRD # | 681 | 682 | 684 | 790 | 791 | 800 | 801 | 804 | 805 | 810 |
|---|---|---|---|---|---|---|---|---|---|---|
| IC$_{50}$ (μM) | 0.74 | 0.57 | 0.53 | 0.70 | 0.64 | 0.66 | 0.47 | 0.31 | 0.23 | 0.43 |

Figure 9

| Kinases | 801 | 802 | 804 | 700 | 701 | 800 | 801 | 804 | 805 | 806 | 807 | 775 | 810 |
|---|---|---|---|---|---|---|---|---|---|---|---|---|---|
| ABL1 | >10000 | 5621.00 | 8341.00 | 468.10 | 3440.00 | 7.16 | 10.20 | 106.80 | 66.90 | 34.08 | 42.00 | 15.70 | 0.87 |
| ABL1 (T315I mutant) | >10000 | >10000 | >10000 | >10000 | >10000 | 177.90 | 194.00 | 4564.00 | 5940.00 | 5160.00 | >10000 | 96.00 | 9.40 |
| Aurora A | >10000 | >10000 | >10000 | 329.45 | >10000 | 9.70 | 41.50 | 79.03 | 175.00 | 14.90 | 110.00 | 815.00 | 7.03 |
| c-Src | 3497.00 | 302.10 | 185.70 | 1.69 | 3.90 | 0.22 | 0.61 | 4.66 | 2.24 | 0.83 | 1.39 | 0.66 | 0.06 |
| JAK2 | >10000 | >10000 | >10000 | >10000 | >10000 | 550.70 | 589.00 | 7463.00 | 4410.00 | >10000 | >10000 | 1190.00 | 223.80 |

INDIRUBIN DERIVATIVES AND USES THEREOF IN TREATING CHRONIC MYELOGENOUS LEUKEMIA

CROSS REFERENCE TO RELATED APPLICATIONS

This application claims the benefit of U.S. Provisional Patent Application No. 61/594,934, filed Feb. 3, 2012; and U.S. Provisional Patent Application No. 61/676,267, filed Jul. 26, 2012, both of which are incorporated herein by reference as if fully set forth herein.

BACKGROUND OF THE INVENTION

Signal Transducer and Activator of Transcription (STAT) proteins have essential functions in normal cytokine signaling and are frequently constitutively activated in human tumor cells (Yu and Jove, 2004). STATs have key roles in regulating cell proliferation, survival, angiogenesis and immune function (Parsons and Parsons, 2004; Yu et al., 2009). One of seven different STAT family members, Stat5, is constitutively activated by non-receptor tyrosine kinases (Herrington et al., 2000; Huang et al., 2002; Klejman et al., 2002; Nieborowska-Skorska et al., 1999; Yu and Jove, 2004). Bcr-Abl, an oncogenic non-receptor tyrosine kinase activated in chronic myelogenous leukemia (CML), induces persistent tyrosyl phosphorylation of Stat5 (Bromberg et al., 1999; Nelson et al., 2006; Quintas-Cardama et al., 2006; Shah et al., 2004; Yu and Jove, 2004). Bcr-Abl kinase cooperates with Src family kinases (SFKs) to activate Stat5 in CML cell transformation (Klejman et al., 2002; Wilson et al., 2002). SFKs, also non-receptor tyrosine kinases, phosphorylate critical cellular substrates such STAT family members, including Stat5, thereby regulating oncogenic signaling pathways (Bromann et al., 2004; Parsons and Parsons, 2004; Silva, 2004; Yu and Jove, 2004). In particular, the SFKs, have been shown to cooperate with Bcr-Abl to activate Stat5 signaling in CML cells (Klejman et al., 2002; Lionberger et al., 2000; Wilson et al., 2002).

STAT signaling is currently being investigated as a new molecular target pathway for human cancer treatment (Yu and Jove, 2004; Yu et al., 2009). In Stat5 signaling, two phosphorylated Stat monomers dimerize through reciprocal phosphotyrosyl-SH2 domain interactions (Bromberg et al., 1999; Yu and Jove, 2004). The phosphorylated Stat5 dimers then translocate to the nucleus and bind to the promoters of specific Stat5 responsive genes (Bromberg et al., 1999; Nelson et al., 2006; Yu and Jove, 2004). Persistent activation of Stat5 has a critical role in cell growth and survival in human hematopoietic malignancies (Carlesso et al., 1996; Yu and Jove, 2004). In contrast, blockade of Stat5 signaling down-regulates these down-stream target genes of Stat5, associated with induction of apoptosis in CML cells (Horita et al., 2000; Shah et al., 2004; Yu and Jove, 2004).

Indirubin is the major active anti-tumor ingredient of a traditional Chinese herbal medicine, Danggui Longhui Wan, which is a mixture of 11 herbal ingredients and used for CML treatment (Xiao et al., 2002). IRDs were shown to inhibit CDK1/cyclin B, CDK2/cyclinA, CDK2/cycling E, GSK 3β and CDK5/p25, leading to cell growth inhibition in human cancer cells (Hoessel et al., 1999; Marko et al., 2001; Vougogiannopoulou et al., 2008). IRDs also inhibit phosphorylation of Stat5 in acute myeloid leukemia cells (Zhou et al., 2009). Recently, it has been demonstrated that IRDs blocked constitutive Stat3 signaling in epithelial tumor cells such as breast and prostate cancer (Nam et al., 2005a).

Previously, clinical studies indicated that indirubin is a promising anticancer therapeutic agent for CML treatment, showing low toxicity (Eisenbrand et al., 2004). However, the mechanism of action of IRDs in CML remains largely unknown. There is a need to develop more indirubin derivatives and uses thereof in treating cancer (e.g. CML).

BRIEF DESCRIPTION OF THE DRAWINGS

FIG. 9—Compound $IC_{50}$ using T315I KCL-22 CML cells for IRDs 681, 682, 684, 790, 791, 800, 801, 804, 805, and 810.

FIG. 10—Kinas assays in vitro using recombinant proteins for IRDs 681, 682, 684, 775, 790, 791, 800, 801, 804~807, and 810.

DETAILED DESCRIPTION OF THE INVENTION

I. Indirubin Derivatives (IRDs)

Figure 1:
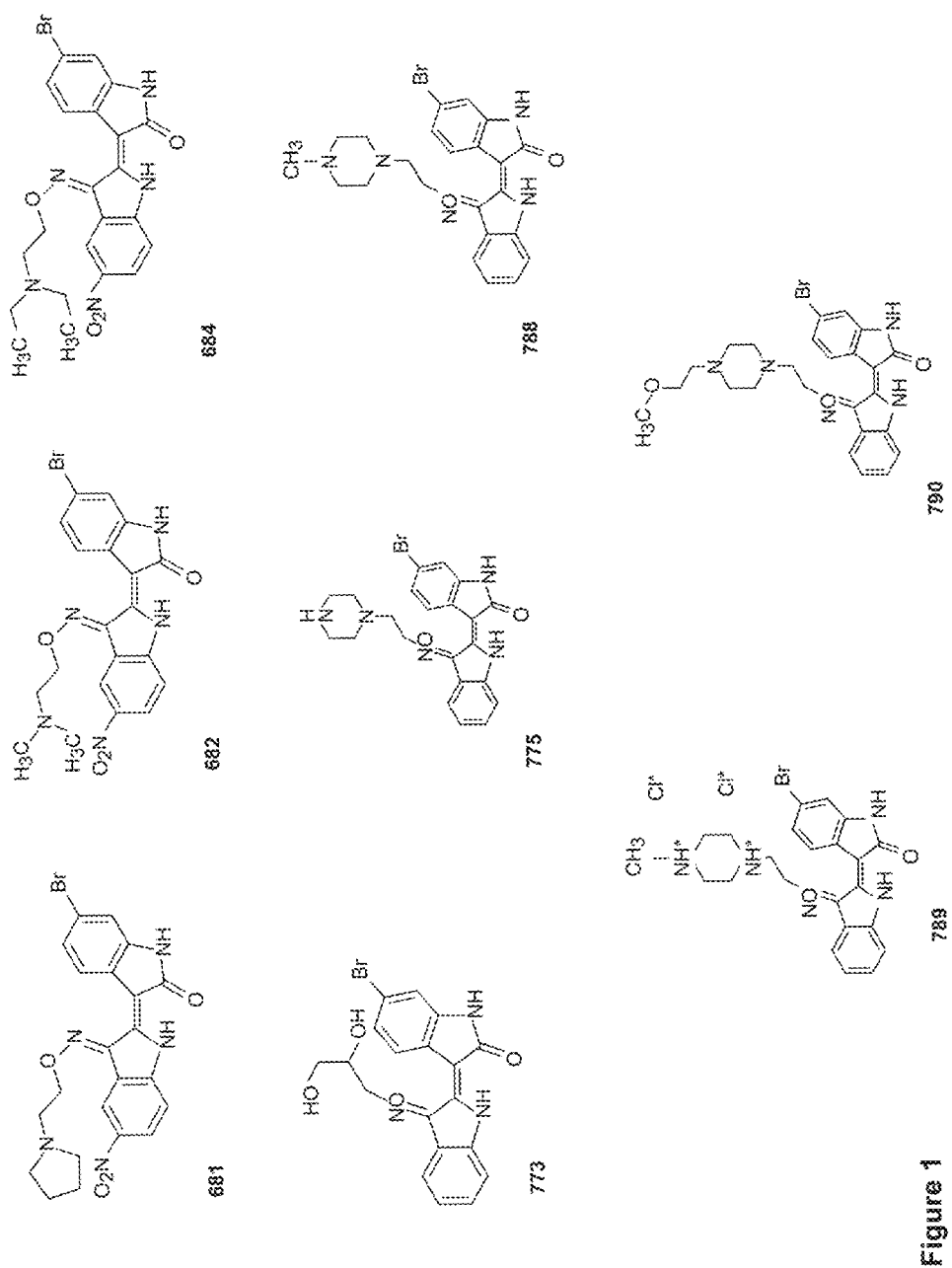
FIG. 1—Structures of IRDs 681, 682, 684, 773, 775, 788~791, 800, 801, 804~807, and 810.
Figure 1:
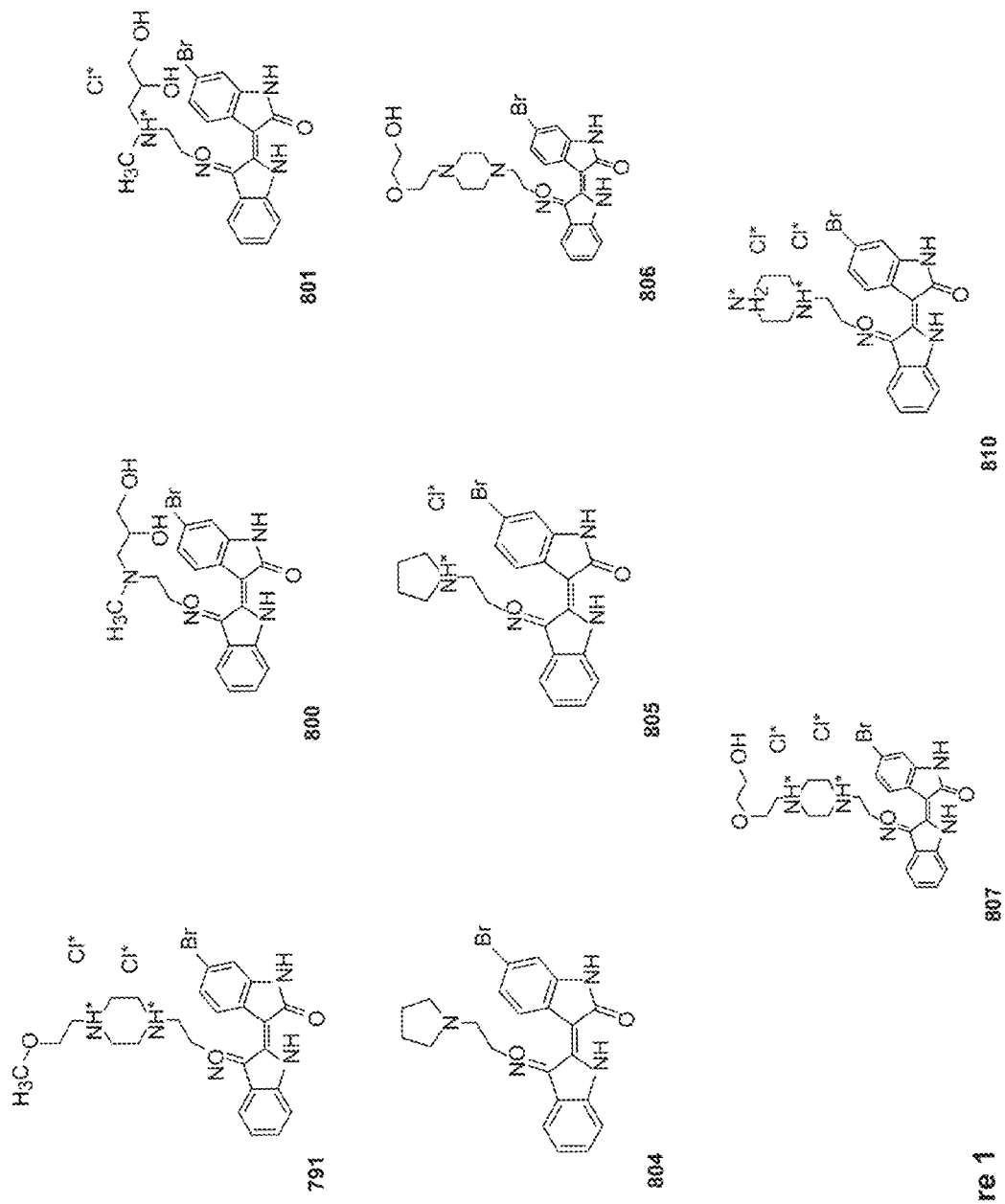
Figure 2:
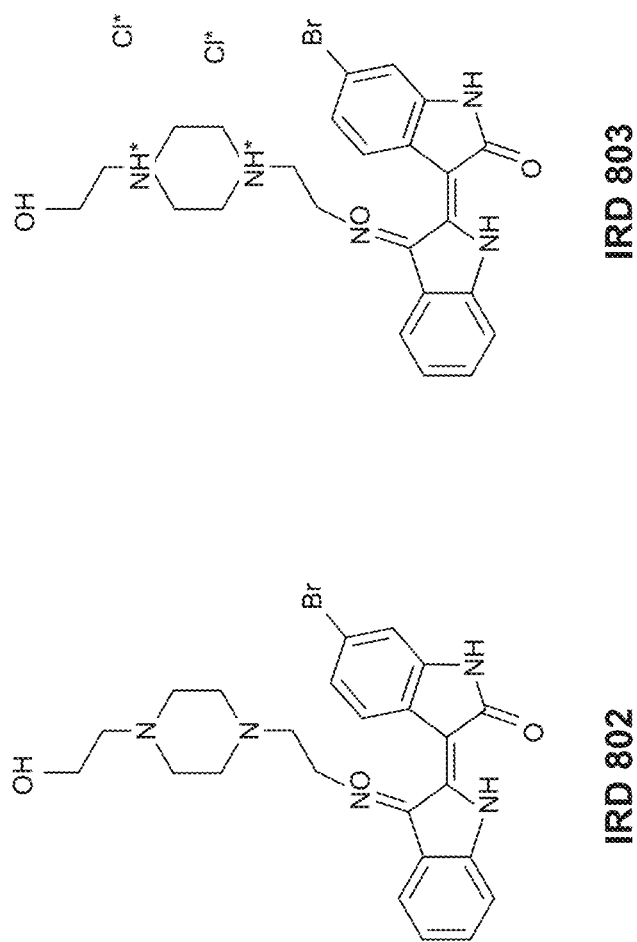
FIG. 2—Structures of IRDs 802 and 803

One aspect of the present disclosure relates to indirubin derivatives (IRDs) IRD 681 (also referred to as 681 or compound 681), IRD 682 (also referred to as 682 or compound 682), IRD 684 (also referred to as 684 or compound 684), IRD 773 (also referred to as 773 or compound 773), IRD 775 (also referred to as 775 or compound 775), IRDs 788~791 (also referred to as 788~791 or compounds 788~791, respectively), IRDs 800~807 (also referred to as 800~807 or compounds 800~807, respectively), and IRD 810 (also referred to as 810 or compound 810) (FIGS. 1 and 2), and the pharmaceutically acceptable derivatives, solvates, salts and stereoisomers thereof, including mixtures thereof in all ratios. Several IRDs are shown as a hydrochloride salt in FIGS. 1, 2 and 6~8. One example of the pharmaceutically acceptable derivatives are the non-salt form of the IRD hydrochloride salts, e.g. the IRDs wherein the amino groups are all or partially neutral. A person of ordinary skill in the art would understand that other suitable inorganic salts and organic salts of the IRDs disclosed herein can also be prepared and used to achieve substantially similar effects. Examples of suitable inorganic acids for the suitable inorganic salts include, but are not limited to, hydrochloric acid, hydrofluoric acid, hydrobromic acid, hydroiodic acid, sulfuric acid and boric acid. Examples of suitable organic acids for the suitable organic salts include, but are not limited to, acetic acid, trifluoroacetic acid, formic acid, oxalic acid, malonic acid, succinic acid, tartaric acid, maleic acid, fumaric acid, methanesulfonic acid, trifluoromethanesulfonic acid, benzoic acid, glycolic acid, lactic acid, citric acid and mandelic acid.

T315I KCL-22 CML cells are imatinib-resistant human KCL-22 CML cells expressing the T315I mutant Bcr-Abl, also referred to as T315I KCL-22 CML (Yuan et al., 2010). T315I KCL-22 CML cells extensively resist over 10 μM of imatinib (Yuan, et al., 2010, JBC), and also appear to resist to dasatinib and nilotinib, which have been approved as the second generation therapy for CML patients.

IRD 684 has shown effects in reducing viabilities of cell lines such as DU145, lymphoma, and T315I KCL-22 CML cell lines.

IRD 804 has shown effects in reducing viabilities of cell lines such as lymphoma, and T315I KCL-22 CML cell lines.

In certain embodiments, IRDs 681, 682, 684, 790, 791, 800, 801, 804~807, and 810 are effective in reducing viabilities of T315I KCL-22 CML cells.

In certain embodiments, IRDs 681, 682, 684, 773, 775, 788~791, 800~807, and 810 are effective in reducing viabilities of KCL-22 CML cells.

In certain embodiments, IRDs 775, 800, 801, 804~807, and 810 are effective in inhibiting Abl1 kinase; IRDs 775, 800, 801 and 810 are effective in inhibiting T315I mutant Abl1 kinase; IRDs 800, 801, 804, 805, 806, 807, and 810 are effective in inhibiting Aurora A kinase; IRDs 684, 775, 790, 791, 800, 801, 804~807, and 810 are effective in inhibiting c-Src kinase; and among the tested IRDs (681, 682, 684, 775, 790, 791, 800, 801, 804~807, and 810), IRD 810 shows the best effect in inhibiting JAK2 kinase (i.e. lowest $IC_{50}$) (FIG. 10). Among the tested IRDs, IRD 810 is the most effective in inhibiting Abl1 kinase, Abl1 kinase (T315I mutant); Aurora A kinase, c-Src kinase and JAK2 kinase.

II. Pharmaceutical Compositions of IRDs

Another aspect of the disclosure relates to a pharmaceutical composition comprising a therapeutically effective amount of at least one IRD disclosed herein.

In certain embodiments, the pharmaceutical composition further comprises a pharmaceutically acceptable carrier.

As used herein, a "therapeutically effective amount," "therapeutically effective concentration" or "therapeutically effective dose" is an amount which, as compared to a corresponding subject who has not received such amount, results in improved treatment, healing, prevention, or amelioration of a disease, disorder, or side effect, or a decrease in the rate of advancement of a disease or disorder.

This amount will vary depending upon a variety of factors, including but not limited to the characteristics of the IRD disclosed herein or pharmaceutical composition thereof (including activity, pharmacokinetics, pharmacodynamics, and bioavailability thereof), the physiological condition of the subject treated (including age, sex, disease type and stage, general physical condition, responsiveness to a given dosage, and type of medication) or cells, the nature of the pharmaceutically acceptable carrier or carriers in the formulation, and the route of administration. Further, an effective or therapeutically effective amount may vary depending on whether the IRD disclosed herein or the pharmaceutical composition thereof is administered alone or in combination with other drug, therapy or other therapeutic method or modality. One skilled in the clinical and pharmacological arts will be able to determine an effective amount or therapeutically effective amount through routine experimentation, namely by monitoring a cell's or subject's response to administration of an IRD disclosed herein or the pharmaceutical composition thereof and adjusting the dosage accordingly. A typical dosage may range from about 0.1 mg/kg to up to about 100 mg/kg or more, depending on the factors mentioned above. In other embodiments, the dosage may range from 0.1 mg/kg up to about 100 mg/kg; or 1 mg/kg up to about 100 mg/kg; or 5 mg/kg up to about 100 mg/kg. For additional guidance, see Remington: The Science and Practice of Pharmacy, 21st Edition, Univ. of Sciences in Philadelphia (USIP), Lippincott Williams & Wilkins, Philadelphia, Pa., 2005, which is hereby incorporated by reference as if fully set forth herein for additional guidance for determining a therapeutically effective amount.

A "pharmaceutically acceptable carrier" is a pharmaceutically-acceptable material, composition or vehicle, such as a liquid or solid filler, diluent, excipient, solvent or encapsulating material, involved in carrying or transporting an active ingredient from one location, body fluid, tissue, organ (interior or exterior), or portion of the body, to another location, body fluid, tissue, organ, or portion of the body. Each carrier is "pharmaceutically acceptable" in the sense of being compatible with the other ingredients, e.g., the IRDs described herein or other ingredients, of the formulation and suitable for use in contact with the tissue or organ of a biological subject without excessive toxicity, irritation, allergic response, immunogenicity, or other problems or complications, commensurate with a reasonable benefit/risk ratio.

Pharmaceutically acceptable carriers are well known in the art and include, without limitation, (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) alcohol, such as ethyl alcohol and propane alcohol; (20) phosphate buffer solutions; and (21) other non-toxic compatible substances employed in pharmaceutical formulations.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of an IRD disclosed herein in these pharmaceutical compositions can vary widely, and will be selected primarily based on fluid volumes, viscosities, body weight and the like in accordance with the particular mode of administration selected and the biological subject's needs. For example, the concentration of an IRD disclosed herein can be 0.0001% to 100%, 0.001% to 50%, 0.01% to 30%, 0.1% to 20%, 1% to 10% wt.

A suitable pharmaceutically acceptable carrier may be selected taking into account the chosen mode of administration, and the physical and chemical properties of the compounds.

One skilled in the art will recognize that a pharmaceutical composition containing an IRD disclosed herein can be administered to a subject by various routes including, without limitation, orally or parenterally, such as intravenously. The composition can be administered by injection or by intubation.

In one embodiment, the pharmaceutical carrier may be a liquid and the pharmaceutical composition would be in the form of a solution. In another embodiment, the pharmaceutically acceptable carrier is a solid and the pharmaceutical composition is in the form of a powder, tablet, pill, or capsules. In another embodiment, the pharmaceutical carrier is a gel and the pharmaceutical composition is in the form of a suppository or cream.

A solid carrier can include one or more substances which may also act as flavoring agents, lubricants, solubilizers, suspending agents, fillers, glidants, compression aids, binders or table-disintegrating agents, it can also be an encapsulating material. In powders, the carrier is a finely divided solid that is in admixture with the finely divided active ingredient. In tablets, the active-ingredient is mixed with a carrier having the necessary compression properties in suitable proportions and compacted in the shape and size desired. The powders and tablets preferably contain up to 99% of an IRD disclosed herein. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Besides containing an effective amount of an IRD described herein the pharmaceutical composition may also include suitable diluents, preservatives, solubilizers, emulsifiers, adjuvant and/or carriers.

The pharmaceutical composition can be administered in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

Additional pharmaceutical compositions will be evident to those skilled in the art, including formulations involving binding agent molecules in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, PCT/US93/0082948 which is incorporated herein by reference as if fully set forth herein for the techniques of controlled release of porous polymeric microparticles for the delivery of pharmaceutical compositions. Additional examples of sustained-release preparations include semipermeable polymer matrices in the form of shaped articles, e.g. films, or microcapsules. Sustained release matrices may include polyesters, hydrogels, polylactides, copolymers of L-glutamic acid and gamma ethyl-L-glutamate, poly(2-hydroxyethyl-methacrylate), ethylene vinyl acetate or poly-D(−)-3-hydroxybutyric acid. Sustained-release compositions also include liposomes, which can be prepared by any of several methods known in the art.

In one embodiment, the present invention is directed to kits for producing a single-dose administration unit. The kits may each contain both a first container having dried components and a second container having a formulation comprising a pharmaceutically acceptable carrier (e.g. an aqueous formulation). Also included within the scope of this invention are kits containing single and multi-chambered pre-filled syringes (e.g., liquid syringes and lyosyringes).

III. Methods of Using IRDs or Pharmaceutical Compositions Thereof

Another aspect of the disclosure relates to a method of treating a cancer in a subject comprising administering to the subject a therapeutically effective amount of at least one IRD disclosed herein or a pharmaceutical composition thereof as disclosed herein.

Optimal dosages to be administered may be determined by those skilled in the art, and will vary with the particular IRD in use, the strength of the preparation, the mode of administration, and the advancement of the disease condition. Additional factors depending on the particular subject being treated, includes, without limitation, subject age, weight, gender, diet, time of administration, time and frequency of administration, drug combination(s), reaction sensitivities, and response to therapy. Administration of the pharmaceutical composition may be effected continuously or intermittently. In any treatment regimen, the pharmaceutical composition may be administered to a subject either singly or in a cocktail containing two or more IRDs, other therapeutic agents, compositions, or the like, including, but not limited to, tolerance-inducing agents, potentiators and side-effect relieving agents. All of these agents are administered in generally-accepted efficacious dose ranges such as those disclosed in the Physician's Desk Reference, 41st Ed., Publisher Edward R. Barnhart, N.J. (1987).47, which is herein incorporated by reference as if fully set forth herein. In certain embodiments, an appropriate dosage level will generally be about 0.001 to 50 mg per kg subject body weight per day that can be administered in single or multiple doses. Preferably, the dosage level will be about 0.005 to about 25 mg/kg, per day; more preferably about 0.01 to about 10 mg/kg per day; and even more preferably about 0.05 to about 1 mg/kg per day.

The frequency of dosing will depend upon the pharmacokinetic parameters of the therapeutic agents in the pharmaceutical composition (e.g. an IRD disclosed herein) used. Typically, a pharmaceutical composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data. Long-acting pharmaceutical compositions may be administered every 3 to 4 days, every week, or biweekly depending on the half-life and clearance rate of the particular formulation.

Examples of the cancer treated in the method include, without limitation, CML, prostate cancer, and lymphoma.

In certain embodiments, the cancer treated is CML. The IRD is selected from the group consisting of IRDs 681, 682, 684, 773, 775, 788~791, 800, 801, 804~807, and 810. The pharmaceutical composition comprises at least one IRD selected from the group consisting of IRDs 681, 682, 684, 773, 775, 788~791, 800, 801, 804~807, and 810.

In certain embodiment the CML treated is a drug (e.g. imatinib, dasatinib and/or nilotinib) resistant CML (e.g. T315I KCL-22 CML). The IRD is selected from the group consisting of IRDs 681, 682, 684, 790, 791, 800, 801, 804~807, and 810. The pharmaceutical composition comprises at least one IRD selected from the group consisting of IRDs 681, 682, 684, 790, 791, 800, 801, 804~807, and 810.

In certain embodiments, the cancer treated is lymphoma. The IRD is selected from the group consisting of IRDs 684 and 804. The pharmaceutical composition comprises at least one IRD selected from the group consisting of IRDs 684 and 804.

In certain embodiments, the cancer treated is prostate cancer. The IRD is IRD 684. The pharmaceutical composition comprises IRD 684.

Another aspect of the invention relates to a method of treating a condition regulated by a protein kinase in a subject comprising administering a therapeutically effective amount of at least one IRD disclosed herein or a pharmaceutical composition thereof as disclosed herein.

In certain embodiments, the protein kinase is selected from the group consisting of Abl1, Abl1 (T315I mutant), Aurora A, c-Src, and JAK2.

In certain embodiments, the protein kinase is Abl1, and the at least one IRD is selected from the group consisting of IRDs 775, 790, 791, 800, 801, 804–807, and 810.

In certain embodiments, the protein kinase is Abl1 (T315I mutant), and the at least one IRD is selected from the group consisting of IRDs 775, 800, 801, and 810.

In certain embodiments, the protein kinase is Aurora A, and the at least one IRD is selected from the group consisting of IRDs 775, 790, 800, 801, 804–807, and 810.

In certain embodiments, the protein kinase is c-Src, and the at least one IRD is selected from the group consisting of IRDs 682, 684, 775, 790, 800, 801, 804–807, and 810.

In certain embodiments, the protein kinase is JAK2, and the at least one IRD is selected from the group consisting of IRDs 800, 801, and 810.

Another aspect of the invention relates to a method of treating CML in a subject comprising administering at least one indirubin derivative compound or a pharmaceutical composition thereof to the subject.

In certain embodiments, the at least one indirubin derivative compound comprises a structure of Structure A:

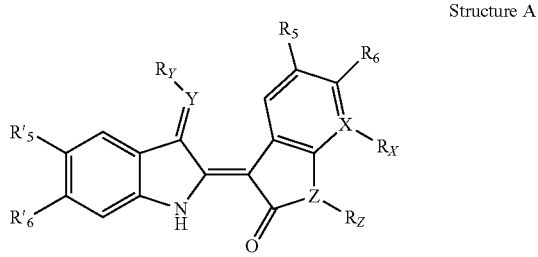

Structure A and the pharmaceutically acceptable solvates, salts and stereoisomers thereof, including mixtures thereof in all ratios, wherein:

X is C or N;
$R_X$ is selected from the group consisting of nothing, H, halogen, and haloalkyl;
$R_6$ is selected from the group consisting of H, halogen, substituted and unsubstituted alkylamino, and substituted and unsubstituted alkoxy;
$R_5$ is selected from the group consisting of H, halogen, nitro, amino, substituted and unsubstituted alkylamino, and substituted and unsubstituted alkyl;
Y is N or O;
when Y is N, $R_Y$ is selected from the group consisting of nothing, H, hydroxy, alkoxy, haloalkoxy, substituted and unsubstituted —O—C(=O)—N(R')R", substituted and unsubstituted —O—C(=O)—$R_0$, and —O—R—R';
when Y is O, $R_Y$ is nothing;
$R'_5$ is selected from the group consisting of H, alkoxy, nitro, —CN, —C(=O)—O—$R_0$, —C(=O)—OH, —C(=O)H, heteroaryl, —C=N—OH and —R—OH;
$R'_6$ is selected from the group consisting of H, halogen, alkyl and —C(=O)—O—$R_0$; more preferably H;
Z is N or S; more preferably N;
$R_Z$ is selected from the group consisting of H, O, —C(=O)—$R_0$, and $R_0$; more preferably H or $R_0$;
each R is independently nothing or substituted or unsubstituted alkylenyl; each $R_0$ is independently substituted or unsubstituted alkyl;
each R' and R" are independently selected from the group consisting of H, substituted and unsubstituted alkyl, substituted and unsubstituted alkoxy, substituted and unsubstituted alkylamino, substituted and unsubstituted haloalkyl, substituted and unsubstituted heterocyclyl, substituted and unsubstituted aryl and substituted and unsubstituted heteroaryl.

EXAMPLES

Example 1

IRDs Inhibited Stat5 Activity

Cell Lines and Reagents

Human KCL-22 CML cells were obtained from the American Type Culture Collection (ATCC). Cells were cultured in RPMI-1640 media containing 10% fetal bovine serum (FBS). Imatinib-resistant human KCL-22 CML cells expressing the T315I mutant Bcr-Abl (KCL-22M) were derived from human KCL-22 CML cells (Yuan et al., 2010). Cells were grown in RPMI 1640 media supplemented with 10% FBS. Monoclonal antibodies to Abl protein and phosphotyrosine (p-Y) were obtained from BD Biosciences (San Diego, Calif.). Polyclonal antibodies to p-Stat5 (Y694) and p-Src family (Y419) were obtained from Cell Signaling Technologies (Cambridge, Mass.). Polyclonal antibodies to Stat5 were from Santa Cruz Biotechnology (Santa Cruz, Calif.). Monoclonal antibody to Src was obtained from Millipore (Billerica, Mass.).

Western Blot Analyses

Western analyses were performed as described previously with minor modification (Nam et al., 2005b). Briefly, KCL-22 CML and T315I KCL-22 CML cells were treated with IRDs. Whole-cell lysates were resolved by SDS-PAGE and immunoblotted with specific antibodies. Primary phospho-specific antibodies were incubated in TBS (pH 7.5) with 0.1% Tween-20 and 5% BSA with gentle agitation overnight at 4° C. Horseradish peroxidase-conjugated secondary antibodies were incubated in TBS (pH 7.5) with 5% nonfat milk and 0.1% Tween-20 at a 1:2000 dilution for 1 hour at room temperature. Positive immuno-reactive proteins were detected using the ECL system (Pierce, Rockford, Ill.).

1a. IRD 810 Reduced Levels of p-Stat5 in CML Cells

Figure 3:
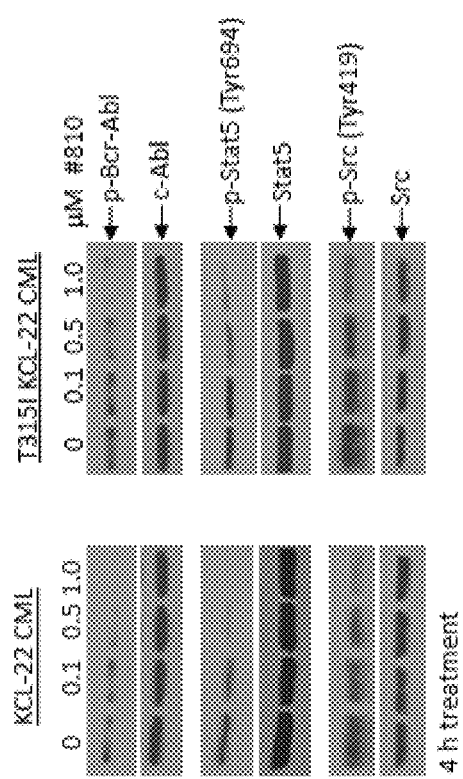
FIG. 3—Effects of compound IRD 810 on Bcr-Abl/Stat5 or Src/Stat5 signaling in KCL-22 CML cells and T315I KCL-22 CML cells (imatinib-resistant human KCL-22 CML cells expressing the T315I mutant Bcr-Abl, also referred to as T315I KCL-22 CML).

Western blot analysis with specific antibodies to p-Stat5 was performed to evaluate the effects of IRD 810 on phosphorylation of Stat5 in KCL-22 CML and T315I KCL-22 CML cells. Cells were treated with IRD 810 in a dose-dependent manner for 4 hours and Western blot analysis was performed using whole-cell lysates as described above. IRD 810 substantially inhibited tyrosyl phosphorylation of Stat5 at 5 μM, whereas total Stat5 levels were unchanged (FIG. 3, middle panels).

It has been shown before that IRDs inhibit Src/Stat3 signaling (Nam et al., 2005a), associated with induction of apoptosis in solid tumor cells. Similarly, these results suggest that IRDs could directly target upstream kinases such as Bcr-Abl and/or SFKs, which constitutively activate Stat5 via tyrosyl phosphorylation of Stat5 at Y694 in chronic leukemias.

1b. IRD 810 Inhibited Tyrosyl Phosphorylation of Src

To examine the effects of 810 on autophosphorylation of Src in KCL-22 CML and T315I KCL-22 CML cells, Western blot analysis was performed with specific antibodies to p-Src and Src as described above. IRD 810 caused strong reduction of autophosphorylation of Src at 1.0 µM in KCL-22 CML and T315I KCL-22 CML cells (FIG. 3, bottom panels).

1c. Effect of IRD 810 on Abl Kinase Activity and Levels of p-Bcr-Abl

To address whether IRD 810 inhibits tyrosyl phosphorylation of endogenous Bcr-Abl in KCL-22 CML and T315I KCL-22 CML cells, Western blot analysis was performed using lysates from the cells treated with IRD 810 in a dose-dependent manner for 4 hours as described above. IRD 810 reduced levels of p-Bcr-Abl at concentrations higher than 0.5 µM in cells (FIG. 3, top panels). Indirubins are known to be ATP competitors and bind to the ATP binding pocket in the catalytic domain of CDKs (Hoessel et al., 1999). Likewise, the inhibitory activity IRD 810 might result from ATP-competitive binding into the Bcr-Abl kinase binding pocket in CML cells.

1d. Discussion

Several synthetic IRDs have shown potent antitumor activities, blocking constitutive Stat3 signaling in human solid tumor cell lines (Nam et al., 2005a). IRD 810 showed strong inhibitory potency against Stat5 signaling in human CML cells.

In comparison of both of Src and Abl kinase activities in vitro, IRD 810 inhibited Abl kinase activity at about 15-fold higher concentration (FIG. 10). In addition, IRD 810 reduced levels of p-Bcr-Abl at higher concentrations in cells (FIG. 3). These findings suggest that IRDs inhibited Src/Stat5 signaling more strongly than Bcr-Abl/Stat5 signaling in CML cells. These effects of IRD 810 could be responsible for induction of apoptosis, suggesting that IRD 810 and other IRDs disclosed herein may have potential as therapeutic agents in drug-resistant CML cells. In particular, IRDs disclosed herein are new therapeutics for wild type or T315I mutant Bcr-Abl-positive CML patients.

Example 2

Effects of IRDs on T315I KCL-22 CML Cells

MTS assays were performed for cell viability as described by the supplier (Promega, Madison, Wis.). T315I KCL-22 CML cells were seeded in 96-well plates (10000/well), and incubated overnight at 37° C. in 5% $CO_2$, and exposed to 1 µM of a test compound (IRDs 681, 682, 684, 773, 790, 791, 800~807, or 810) for 48 hours. Dimethyl sulfoxide (DMSO) was used as the vehicle control. Viable cell numbers were determined by tetrazolium conversion to its formazan dye and absorbance was measured at 490 nm using an automated ELISA plate reader. Each experiment was performed in duplicate. Data are shown in mean (FIG. 4).

Figure 4:
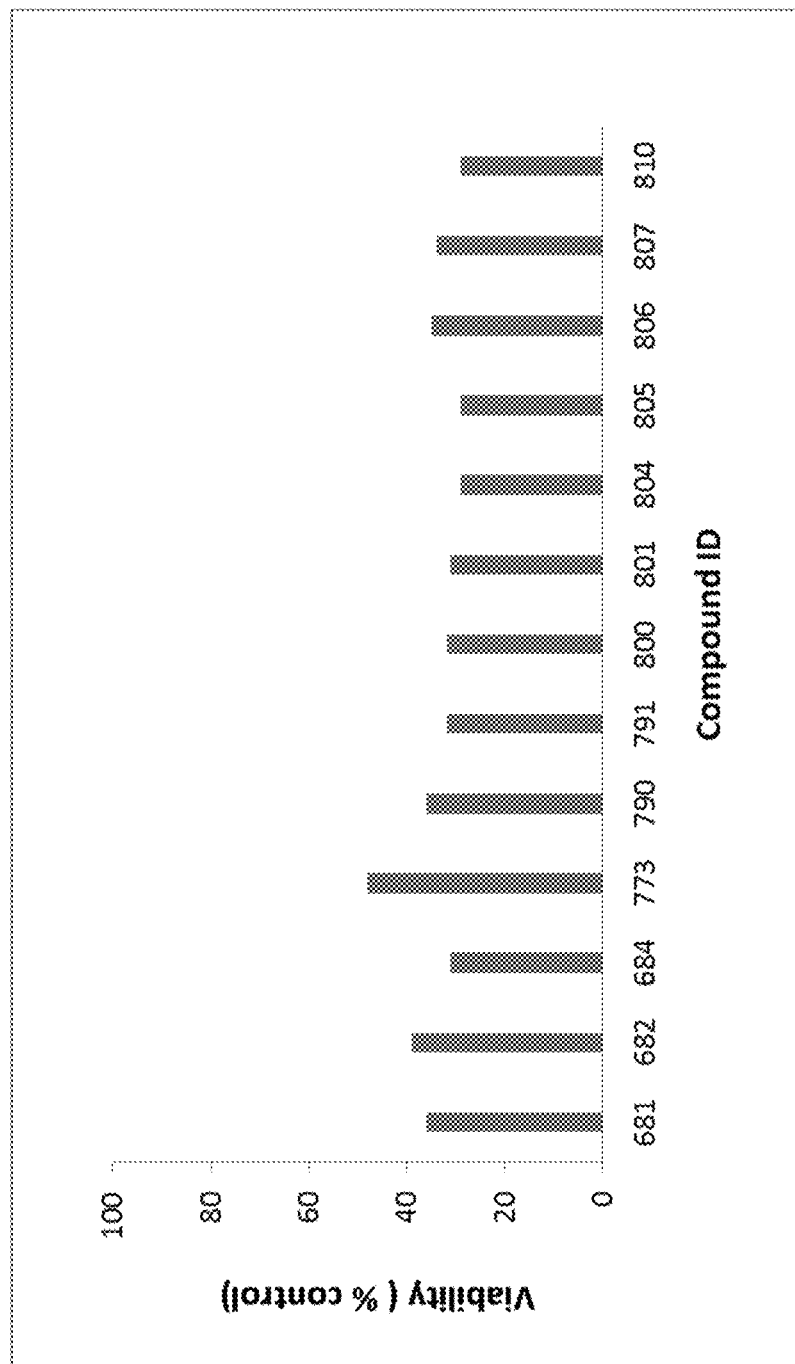
FIG. 4—Effects of IRDs 681, 682, 684, 773, 790, 791, 800, 801, 804~807, and 810 on viabilities of T315I KCL-22 CML cells at 1 µM concentration of the tested IRDs.

Several test compounds (IRDs 681, 682, 684, 790, 791, 800, 801, 804~807, 810) showed approximately 60%~75% loss of cell viabilities of these mutant cells at 1 µM concentration (FIG. 4). IRD 773 showed approximately 50% loss of cell viabilities of these mutant cells at 1 µM concentration (FIG. 4).

Example 3

Effects of IRDs on KCL-22 CML Cells

Figure 5:
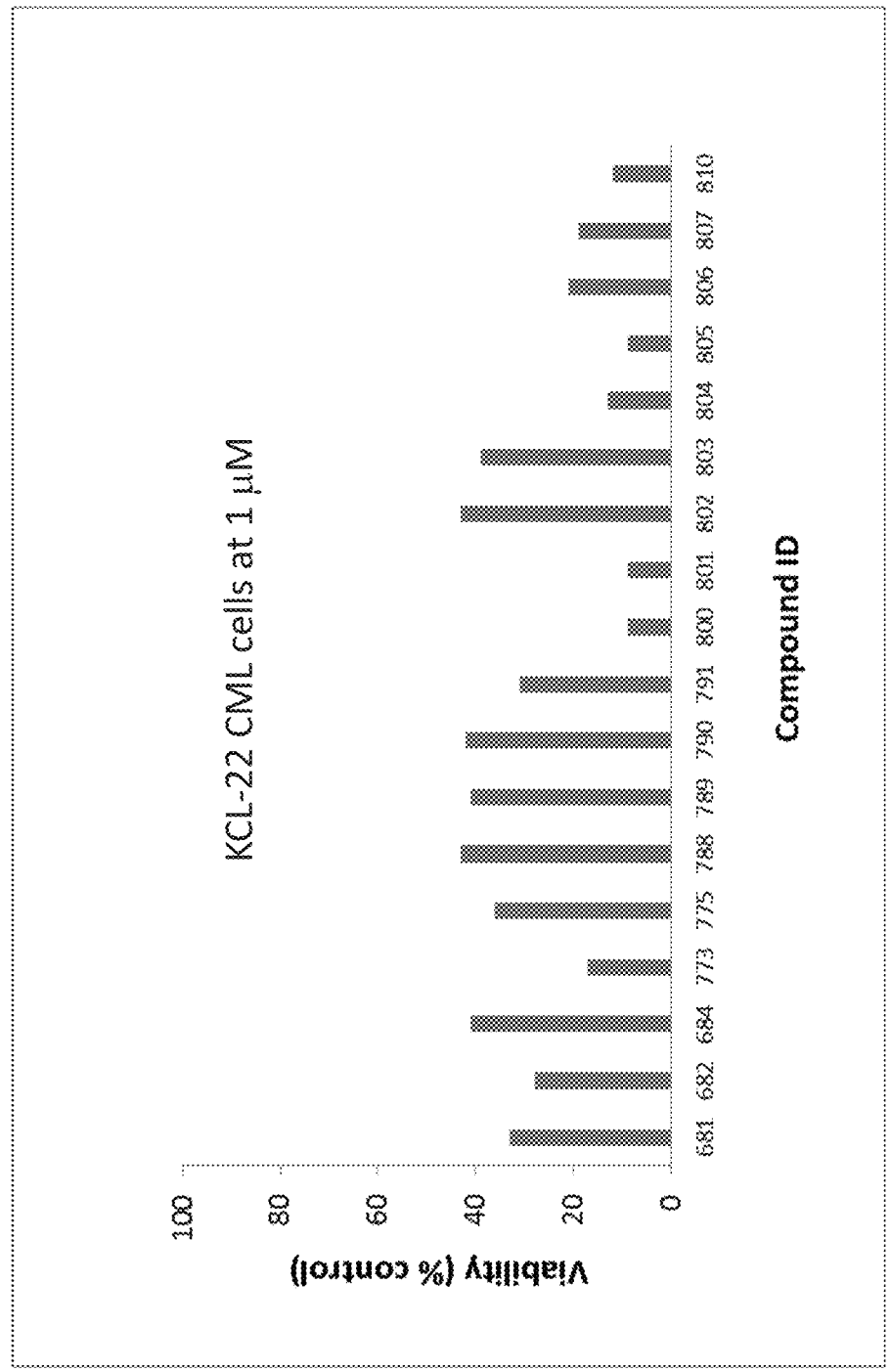
FIG. 5—Effects of IRDs 681, 682, 684, 773, 775, 788~791, 800~807, and 810 on viabilities of KCL-22 CML cells at 1 µM concentration of the tested IRDs.
Figure 6:
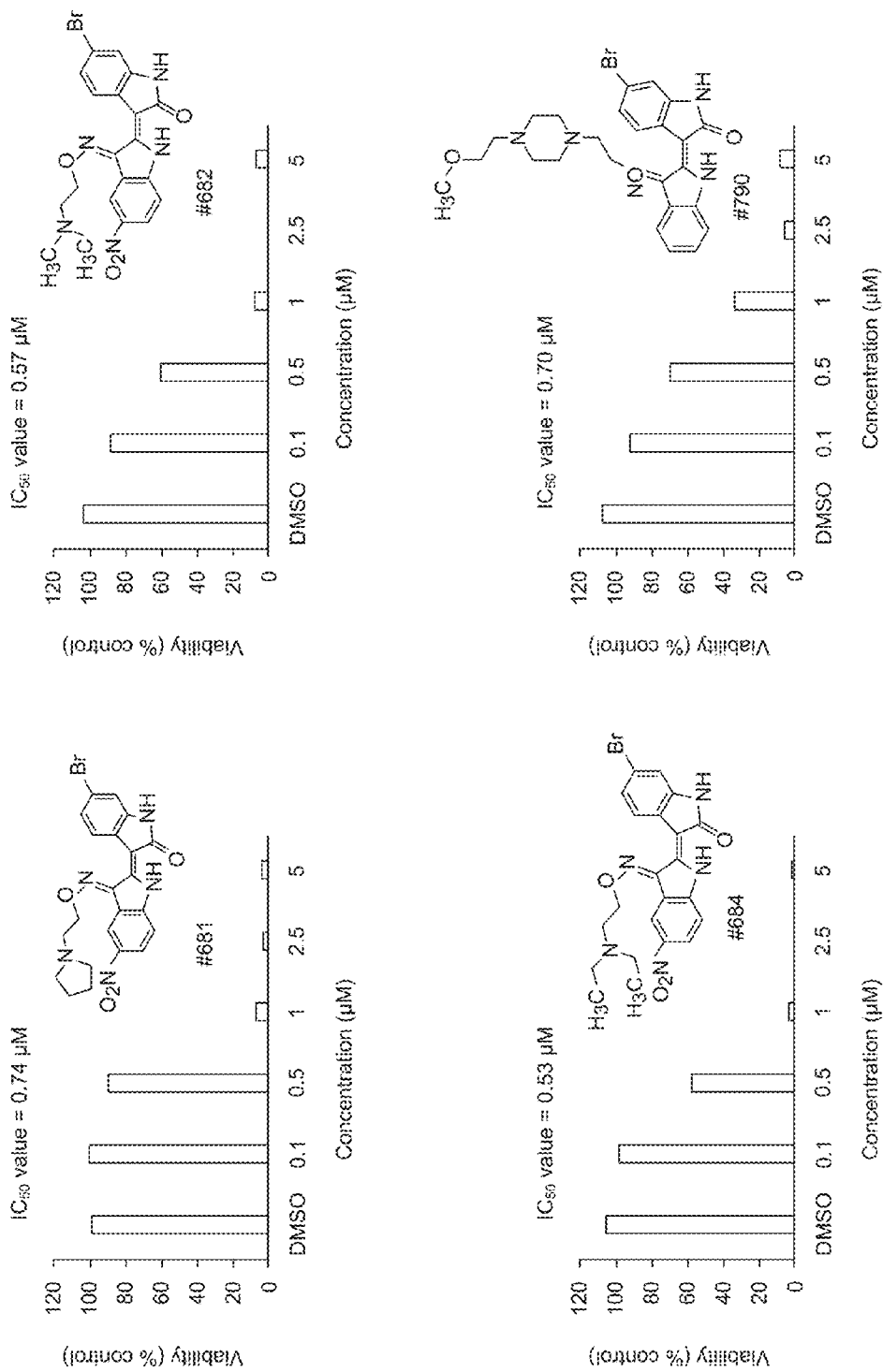
FIG. 6—Determination of $IC_{50}$ using T315I KCL-22 CML cells for IRDs 681, 682, 684, and 790.
Figure 7:
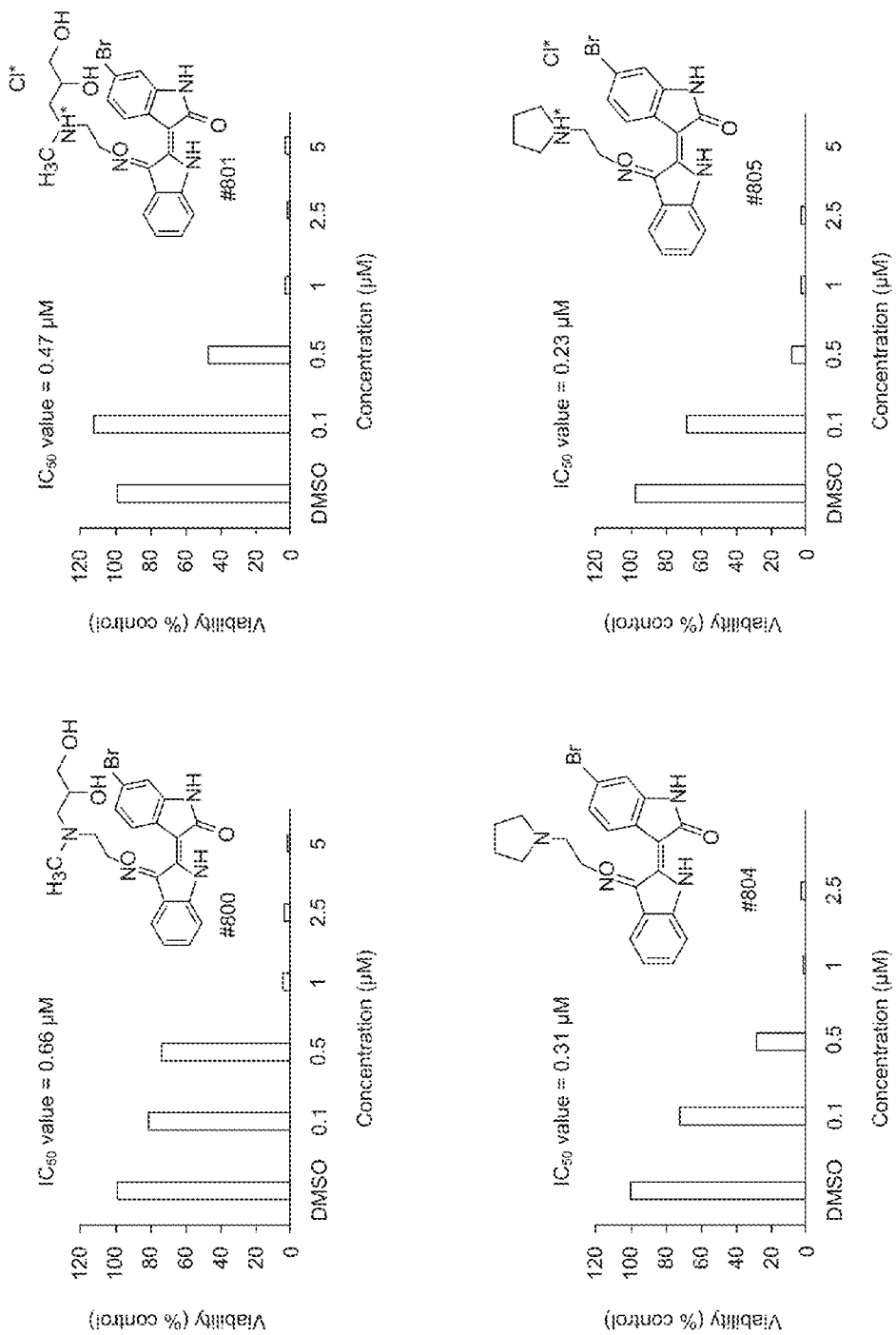
FIG. 7—Determination of $IC_{50}$ using T315I KCL-22 CML cells for IRDs 800, 801, 804, and 805.
Figure 8:
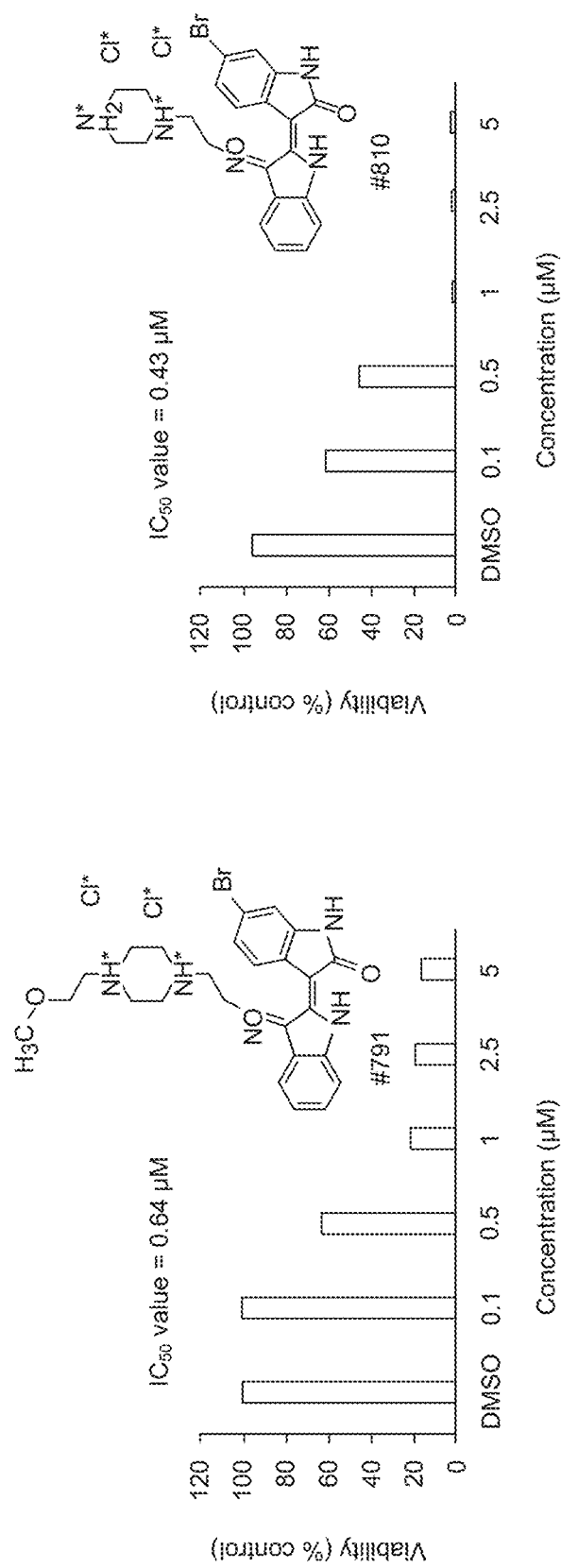
FIG. 8—Determination of $IC_{50}$ using T315I KCL-22 CML cells for IRDs 791 and 810.

MTS assays were performed for cell viability. KCL-22 CML cells were seeded in 96-well plates (10000/well) and exposed to 1 µM of IRDs 681, 682, 684, 773, 775, 788~791, 800~807, or 810 for 48 hours. Dimethyl sulfoxide (DMSO) was used as the vehicle control. Viable cell numbers were determined by tetrazolium conversion to its formazan dye and absorbance was measured at 490 nm using an automated ELISA plate reader. Each experiment was performed in duplicate. Data were mean of the duplicate experiments. KCL-22 CML cells showed approximately 60%~90% loss of cell viabilities after treated with IRDs 681, 682, 684, 773, 775, 788~791, 800~807, or 810 as described supra (FIG. 5). KCL-22 CML cells showed approximately 80% loss of cell viabilities after treated with IRDs 682, 773, 800~807, or 810 as described supra (FIG. 5).

Example 4

Determination of $IC_{50}$ of IRDs on T315I KCL-22 CML Cell

MTS assays were performed for cell viability. T315I KCL-22 CML cells were seeded in 96-well plates (10000/well) and exposed to an IRD (IRD 681, 682, 684, 790, 791, 800, 801, 804, 805, or 810) in a dose-dependent manner (0.1 µM, 0.5 µM, 1 µM, 2.5 µM, and 5 µM) for 48 hours. DMSO was used as the vehicle control. Viable cell numbers were determined by tetrazolium conversion to its formazan dye and absorbance was measured at 490 nm using an automated ELISA plate reader. Each experiment was performed in quadruplicate. Data are shown in mean (FIGS. 6-9).

Example 5

In Vitro Kinase Assays of IRDs Using Recombinant Proteins

The in vitro kinase assays of an IRD (681, 682, 684, 775, 790, 791, 800, 801, 804~807, or 810) was carried out using recombinant proteins. The proteins, freshly prepared substrates and $^{33}$P-ATP (specific activity 0.01 µCi/µl final) were mixed in a reaction buffer (20 mM HEPES pH 7.5, 10 mM $MgCl_2$, 1 mM EGTA, 0.02% Brij35, 0.02 mg/ml BSA, 0.1 mM $Na_3VO_4$, 2 mM DTT) in the presence of DMSO as control or a test IRD. The mixtures were reacted for 120 min at room temperature. Samples were transferred onto P81 ion exchange paper and filters were extensively washed with 0.75% phosphoric acid. The radioactivities were monitored. The results are summarized in FIG. 10.

Among the IRDs tested in this example, IRD 810 shows the lowest $IC_{50}$ for kinases Abl1, Abl1 (T315I mutant), Aurora A, c-Src and JAK2.

The tested IRDs showed a higher $IC_{50}$ for Abl1 with T315I mutant. For Abl1 kinase, IRDs 775, 790, 800, 801, 804, 805, 806, 807, and 810 showed a less than about 500 nM $IC_{50}$, IRDs 775, 800, 801, 804, 805, 806, 807, and 810 showed a less than about 110 nM $IC_{50}$, IRDs 800, 801 and 810 had $IC_{50}$ of about 10 nM or less, and IRD 801 had $IC_{50}$ of less than 1 nM.

For Abl1 with T315I mutant, IRDs 775, 800, 801, and 810 showed $IC_{50}$ of about 200 nM or less, IRDs 775 and 810 showed $IC_{50}$ of about 100 nM or less, and IRD 810 showed $IC_{50}$ of 9.40 nM.

For Aurora A kinase, IRDs 790, 800, 801, 804~807 and 810 showed $IC_{50}$ of about 350.00 nM or less, IRDs 800, 801, 804~807 and 810 showed $IC_{50}$ of about 175.00 nM or less, IRDs 800, 806, and 810 showed $IC_{50}$ of about 15 nM or less, and IRDs 800 and 810 showed $IC_{50}$ of less than 10 nM.

Among the kinases tested, the tested IRDs showed the lowest $IC_{50}$ for c-Src kinase. IRDs 682, 684, 775, 790, 791, 800, 801, 804~807 and 810 showed $IC_{50}$ of about 300 nM or less, IRDs 775, 790, 791, 800, 801, 804~807 and 810 showed $IC_{50}$ of about 5 nM or less, IRDs 775, 790, 800, 801, 805~807 and 810 showed $IC_{50}$ of about 2 nM or less, and IRDs 775, 800, 801, 806, and 810 showed $IC_{50}$ of about 1 nM or less.

Among the kinases tested, the tested IRDs showed the highest $IC_{50}$ for JAK2 kinase. IRDs 800, 801, and 810 showed $IC_{50}$ of about 600 nM or less, and IRD 810 showed $IC_{50}$ of 223.80 nM.

The references cited in this application and listed below are incorporated herein by reference as if fully set forth herein:

Aichberger, K. J., Mayerhofer, M., Krauth, M. T., Skvara, H., Florian, S., Sonneck, K., Akgul, C., Derdak, S., Pickl, W. F., Wacheck, V., Selzer, E., Monia, B. P., Moriggl, R., Valent, P., Sillaber, C., 2005. Identification of mcl-1 as a BCR/ABL-dependent target in chronic myeloid leukemia (CML): evidence for cooperative antileukemic effects of imatinib and mcl-1 antisense oligonucleotides. Blood 105, 3303-3311.

Benekli, M., Baer, M. R., Baumann, H., Wetzler, M., 2003. Signal transducer and activator of transcription proteins in leukemias. Blood 101, 2940-2954.

Bromann, P. A., Korkaya, H., Courtneidge, S. A., 2004. The interplay between Src family kinases and receptor tyrosine kinases. Oncogene 23, 7957-7968.

Bromberg, J. F., Wrzeszczynska, M. H., Devgan, G., Zhao, Y., Pestell, R. G., Albanese, C., Darnell, J. E., Jr., 1999. Stat3 as an oncogene. Cell 98, 295-303.

Buettner, R., Mora, L. B., Jove, R., 2002. Activated STAT signaling in human tumors provides novel molecular targets for therapeutic intervention. Clin Cancer Res 8, 945-954.

Carlesso, N., Frank, D. A., Griffin, J. D., 1996. Tyrosyl phosphorylation and DNA binding 17 activity of signal transducers and activators of transcription (STAT) proteins in hematopoietic cell lines transformed by Bcr/Abl. J Exp Med 183, 811-820.

Donato, N. J., Wu, J. Y., Stapley, J., Gallick, G., Lin, H., Arlinghaus, R., Talpaz, M., 2003. BCR-ABL independence and LYN kinase overexpression in chronic myelogenous leukemia cells selected for resistance to ST1571. Blood 101, 690-698.

Eisenbrand, G., Hippe, F., Jakobs, S., Muehlbeyer, S., 2004. Molecular mechanisms of indirubin and its derivatives: novel anticancer molecules with their origin in traditional Chinese phytomedicine. J Cancer Res Clin Oncol 130, 627-635.

Gesbert, F., Griffin, J. D., 2000. Bcr/Abl activates transcription of the Bcl-X gene through STAT5. Blood 96, 2269-2276.

Haura, E. B., Turkson, J., Jove, R., 2005. Mechanisms of disease: Insights into the emerging role of signal transducers and activators of transcription in cancer. Nat Clin Pract Oncol 2, 315-324.

Herrington, J., Smit, L. S., Schwartz, J., Carter-Su, C., 2000. The role of STAT proteins in growth hormone signaling. Oncogene 19, 2585-2597.

Hoessel, R., Leclerc, S., Endicott, J. A., Nobel, M. E., Lawrie, A., Tunnah, P., Leost, M., Damiens, E., Marie, D., Marko, D., Niederberger, E., Tang, W., Eisenbrand, G., Meijer, L., 1999. Indirubin, the active constituent of a Chinese antileukaemia medicine, inhibits cyclin-dependent kinases. Nat Cell Biol 1, 60-67.

Holtz, M. S., Slovak, M. L., Zhang, F., Sawyers, C. L., Forman, S. J., Bhatia, R., 2002. Imatinib mesylate (STI571) inhibits growth of primitive malignant progenitors in chronic myelogenous leukemia through reversal of abnormally increased proliferation. Blood 99, 3792-3800.

Horita, M., Andreu, E. J., Benito, A., Arbona, C., Sanz, C., Benet, I., Prosper, F., Fernandez-Luna, J. L., 2000. Blockade of the Bcr-Abl kinase activity induces apoptosis of chronic myelogenous leukemia cells by suppressing signal transducer and activator of transcription 5-dependent expression of Bcl-xL. J Exp Med 191, 977-984.

Huang, M., Dorsey, J. F., Epling-Burnette, P. K., Nimmanapalli, R., Landowski, T. H., Mora, L. B., Niu, G., Sinibaldi, D., Bai, F., Kraker, A., Yu, H., Moscinski, L., Wei, S., Djeu, J., Dalton, W. S., Bhalla, K., Loughran, T. P., Wu, J., Jove, R., 2002. Inhibition of Bcr-Abl kinase activity by PD180970 blocks constitutive activation of Stat5 and growth of CML cells. Oncogene 21, 8804-8816.

Klejman, A., Schreiner, S. J., Nieborowska-Skorska, M., Slupianek, A., Wilson, M., Smithgall, T. E., Skorski, T., 2002. The Src family kinase Hck couples BCR/ABL to STAT5 activation in myeloid leukemia cells. Embo J 21, 5766-5774.

Konig, H., Copland, M., Chu, S., Jove, R., Holyoake, T. L., Bhatia, R., 2008. Effects of dasatinib on SRC kinase activity and downstream intracellular signaling in primitive chronic myelogenous leukemia hematopoietic cells. Cancer Res 68, 9624-9633.

Lionberger, J. M., Wilson, M. B., Smithgall, T. E., 2000. Transformation of myeloid leukemia cells to cytokine independence by Bcr-Abl is suppressed by kinasedefective Hck. The Journal of biological chemistry 275, 18581-18585.

Marko, D., Schatzle, S., Friedel, A., Genzlinger, A., Zankl, H., Meijer, L., Eisenbrand, G., 2001. Inhibition of cyclin-dependent kinase 1 (CDK1) by indirubin derivatives in human tumour cells. Br J Cancer 84, 283-289.

Nam, S., Buettner, R., Turkson, J., Kim, D., Cheng, J. Q., Muehlbeyer, S., Hippe, F., Vatter, S., Merz, K. H., Eisenbrand, G., Jove, R., 2005a. Indirubin derivatives inhibit Stat3 signaling and induce apoptosis in human cancer cells. Proc Natl Acad Sci USA 102, 5998-6003.

Nam, S., Kim, D., Cheng, J. Q., Zhang, S., Lee, J. H., Buettner, R., Mirosevich, J., Lee, F. Y., Jove, R., 2005b. Action of the Src family kinase inhibitor, dasatinib (BMS-354825), on human prostate cancer cells. Cancer Res 65, 9185-9189.

Nam, S., Williams, A., Vultur, A., List, A., Bhalla, K., Smith, D., Lee, F. Y., Jove, R., 2007. Dasatinib (BMS-354825) inhibits Stat5 signaling associated with apoptosis in chronic myelogenous leukemia cells. Mol Cancer Ther 6, 1400-1405.

Nelson, E. A., Walker, S. R., Li, W., Liu, X. S., Frank, D. A., 2006. Identification of human STAT5-dependent gene regulatory elements based on interspecies homology. The Journal of biological chemistry 281, 26216-26224.

Nieborowska-Skorska, M., Wasik, M. A., Slupianek, A., Salomoni, P., Kitamura, T., Calabretta, B., Skorski, T., 1999. Signal transducer and activator of transcription (STAT)5 activation by BCR/ABL is dependent on intact Src homology (SH)3 and SH2 domains of BCR/ABL and is required for leukemogenesis. J Exp Med 189, 1229-1242.

Parsons, S. J., Parsons, J. T., 2004. Src family kinases, key regulators of signal transduction. Oncogene 23, 7906-7909.

Ptasznik, A., Nakata, Y., Kalota, A., Emerson, S. G., Gewirtz, A. M., 2004. Short interfering RNA (siRNA) targeting the Lyn kinase induces apoptosis in primary, and drug-resistant, BCR-ABL1(+) leukemia cells. Nat Med 10, 1187-1189.

Quintas-Cardama, A., Kantarjian, H., Jones, D., Nicaise, C., O'Brien, S., Giles, F., Talpaz, M., Cortes, J., 2007. Dasatinib (BMS-354825) is active in Philadelphia chromosome-positive chronic myelogenous leukemia after imatinib and nilotinib (AMN107) therapy failure. Blood 109, 497-9

Shah, N. P., Tran, C., Lee, F. Y., Chen, P., Norris, D., Sawyers, C. L., 2004. Overriding imatinib resistance with a novel ABL kinase inhibitor. Science 305, 399-401.

Silva, C. M., 2004. Role of STATs as downstream signal transducers in Src family inasemediated tumorigenesis. Oncogene 23, 8017-8023.

Vougogiannopoulou, K., Ferandin, Y., Bettayeb, K., Myrianthopoulos, V., Lozach, O., Fan, Y., Johnson, C. H., Magiatis, P., Skaltsounis, A. L., Mikros, E., Meijer, L., 2008. Soluble 3',6-substituted indirubins with enhanced selectivity toward glycogen synthase kinase −3 alter circadian period. J Med Chem 51, 6421-6431.

Wilson, M. B., Schreiner, S. J., Choi, H. J., Kamens, J., Smithgall, T. E., 2002. Selective pyrrolo-pyrimidine inhibitors reveal a necessary role for Src family kinases in Bcr-Abl signal transduction and oncogenesis. Oncogene 21, 8075-8088.

Wu, J., Meng, F., Lu, H., Kong, L., Bornmann, W., Peng, Z., Talpaz, M., Donato, N. J., 2008. Lyn regulates BCR-ABL and Gab2 tyrosine phosphorylation and c-Cbl protein stability in imatinib-resistant chronic myelogenous leukemia cells. Blood 111, 3821-3829.

Xiao, Z., Hao, Y., Liu, B., Qian, L., 2002. Indirubin and meisoindigo in the treatment of chronic myelogenous leukemia in China. Leuk Lymphoma 43, 1763-1768.

Yu, H., Jove, R., 2004. The STATs of cancer—new molecular targets come of age. Nat Rev Cancer 4, 97-105.

Yu, H., Pardoll, D., Jove, R., 2009. STATs in cancer inflammation and immunity: a leading role for STAT3. Nat Rev Cancer 9, 798-809.

Yuan, H., Wang, Z., Gao, C., Chen, W., Huang, Q., Yee, J. K., Bhatia, R., 2010. BCRABL gene expression is required for its mutations in a novel KCL-22 cell culture model for acquired resistance of chronic myelogenous leukemia. The Journal of biological chemistry 285, 5085-5096.

Zhou, J., Bi, C., Janakakumara, J. V., Liu, S. C., Chng, W. J., Tay, K. G., Poon, L. F., Xie, Z., Palaniyandi, S., Yu, H., Glaser, K. B., Albert, D. H., Davidsen, S. K., Chen, C. S., 2009. Enhanced activation of STAT pathways and overexpression of survivin confer resistance to FLT3 inhibitors and could be therapeutic targets in AML. Blood 113, 4052-4062.

The invention claimed is:

1. An IRD selected from the group consisting of IRDs 681, 682, and 684, and the pharmaceutically acceptable derivatives, solvates, salts and stereoisomers thereof, including mixtures thereof in all ratios:

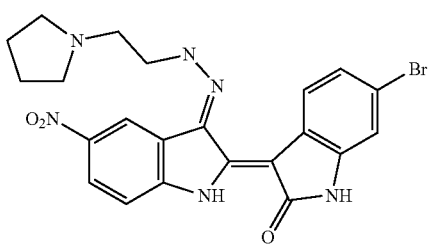

681

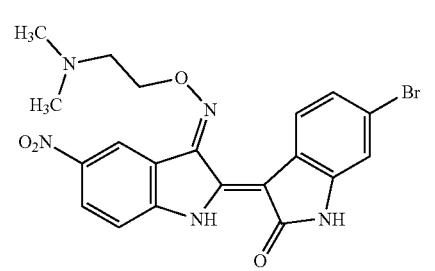

682

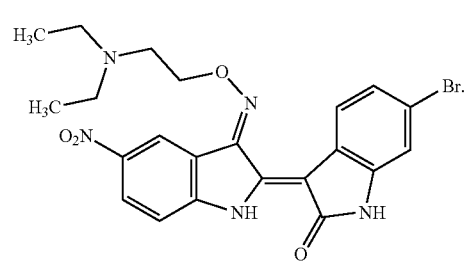

684

2. A pharmaceutical composition comprising a therapeutically effective amount of at least one IRD according to claim 1.

3. The pharmaceutical composition according to claim 2, further comprising a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 9,512,076 B2 | Page 1 of 1 |
| APPLICATION NO. | : 13/758921 | |
| DATED | : December 6, 2016 | |
| INVENTOR(S) | : Richard Jove et al. | |

It is certified that error appears in the above-identified patent and that said Letters Patent is hereby corrected as shown below:

In the Specification

Column 1, Line 13 Please add a Government Interest section:
--This invention was made with government support under R01 CA115674 awarded by the National Institutes of Health. The government has certain rights in the invention.--

Signed and Sealed this
Ninth Day of January, 2024

*Katherine Kelly Vidal*

Katherine Kelly Vidal
*Director of the United States Patent and Trademark Office*